US009645041B2

(12) United States Patent
Mars

(10) Patent No.: US 9,645,041 B2
(45) Date of Patent: May 9, 2017

(54) INTERPOLATION ENGINE FOR ANALYSIS OF TIME-VARYING LOAD DATA SIGNALS

(71) Applicant: Endurica LLC, Findlay, OH (US)

(72) Inventor: William V. Mars, Findlay, OH (US)

(73) Assignee: Endurica LLC, Findlay, OH (US)

( * ) Notice: Subject to any disclaimer, the term of this patent is extended or adjusted under 35 U.S.C. 154(b) by 661 days.

(21) Appl. No.: 13/760,169

(22) Filed: Feb. 6, 2013

(65) Prior Publication Data
US 2013/0204541 A1 Aug. 8, 2013

Related U.S. Application Data

(60) Provisional application No. 61/595,329, filed on Feb. 6, 2012.

(51) Int. Cl.
*G01M 5/00* (2006.01)
*G01N 22/00* (2006.01)

(52) U.S. Cl.
CPC ............ *G01M 5/0033* (2013.01); *G01M 5/00* (2013.01); *G01M 5/0041* (2013.01); *G01N 22/00* (2013.01); *G01N 2203/0069* (2013.01); *G01N 2203/0071* (2013.01); *G01N 2203/0075* (2013.01); *G01N 2203/0216* (2013.01); *G01N 2291/0235* (2013.01); *G01N 2291/0258* (2013.01)

(58) Field of Classification Search
CPC .... G01M 5/00; G01M 5/0033; G01M 5/0041; G01N 2291/0258; G01N 2291/0231; G01N 2203/0216; G01N 22/00; G01N 2291/0235; G01N 2203/0069; G01N 2203/0071; G01N 2203/0075

USPC .......................................................... 702/34
See application file for complete search history.

(56) References Cited

U.S. PATENT DOCUMENTS

| 4,419,480 A | * | 12/1983 | Tabar ...................... C08L 21/00 524/525 |
| 4,764,882 A | | 8/1988 | Braschel et al. |
| 6,634,236 B2 | | 10/2003 | Mars |

(Continued)

OTHER PUBLICATIONS

Conle, F.A., & C-C. Chu, "Fatigue analysis and the local stress-strain approach in complex vehicular structures.", International journal of fatigue 19.93, 1997, 317-323.

(Continued)

*Primary Examiner* — Jonathan C Teixeira Moffat
*Assistant Examiner* — Lynda Dinh
(74) *Attorney, Agent, or Firm* — Ward Law Office LLC; Jacob M. Ward

(57) ABSTRACT

A method for analyzing fatigue life of an elastomeric component includes a step of conducting a finite element analysis to obtain a base state. A plurality of case vectors are then selected to represent a space of possible loading states that occur within a time-varying load data signal based on measurement of the elastomeric component or on a simulation of multibody dynamics. For at least a portion of the case vectors, a finite element analysis is conducted at a plurality of discrete gridpoints along the case vectors starting at the base state and tracking the case vector. Using an interpolation engine, desired local solution variables for a current state may be interpolated from the finite element analysis at the plurality of discrete gridpoints. A damage calculation may then be calculated based on the desired local solution variables for the current state.

13 Claims, 6 Drawing Sheets

(56) References Cited

U.S. PATENT DOCUMENTS

| | | | |
|---|---|---|---|
| 7,321,365 B2 * | 1/2008 | Brombolich | G06F 17/5018 |
| | | | 345/419 |
| 7,363,805 B2 | 4/2008 | Jayakumar et al. | |
| 8,560,288 B2 * | 10/2013 | Imai | G06F 17/5009 |
| | | | 703/7 |
| 2004/0254772 A1 | 12/2004 | Su | |
| 2008/0027693 A1 * | 1/2008 | Khandoker | B29C 35/0222 |
| | | | 703/7 |

OTHER PUBLICATIONS

Yim, Hong Jae, and Sang Beom Lee, "An integrated CAE system for dynamic stress and fatigue life prediction of mechanical systems.", Journal of Mechanical Science and Technology 10.2, 1996, 158-168.

Conle, F.A., & C.W. Mousseau, "Using vehicle dynamics simulations and finite-element results to generate fatigue life contours for chassis components.", International journal of fatigue 13.3, 1991, 195-205.

\* cited by examiner

INTERPOLATION ENGINE FOR ANALYSIS OF TIME-VARYING LOAD DATA SIGNALS

CROSS REFERENCE TO RELATED APPLICATIONS

This application claims the benefit of U.S. Provisional Application No. 61/595,329, filed on Feb. 6, 2012. The entire disclosure of the above application is hereby incorporated herein by reference.

FIELD OF THE INVENTION

The present disclosure relates to a method and system for analyzing fatigue life of elastomeric or rubber components.

BACKGROUND OF THE INVENTION

Solutions for fatigue analysis from finite element analysis (FEA) of metallic components have been available for many years. An important part of the analysis for linear structures such as metallic components is a procedure called "scale and combine", which allows one to convert from raw road load data to stresses and strains. In this procedure, a series of unit load cases is modeled in FEA and can then be used to reconstruct stress or strain histories for a multiaxial input signal.

Nonlimiting examples of fatigue analysis solutions for metallic components are described in each of: Conle, F. A., and C-C. Chu. "Fatigue analysis and the local stress-strain approach in complex vehicular structures." International journal of fatigue 19.93 (1997): 317-323; Braschel, Reinhold, Manfred Miksch, and Rolf Schiffer. "Method of monitoring fatigue of structural component parts, for example, in nuclear power plants." U.S. Pat. No. 4,764,882. 16 Aug. 1988; Yim, Hong Jae, and Sang Beom Lee. "An integrated CAE system for dynamic stress and fatigue life prediction of mechanical systems." Journal of Mechanical Science and Technology 10.2 (1996): 158-168; and Conle, F. A., and C. W. Mousseau. "Using vehicle dynamics simulations and finite-element results to generate fatigue life contours for chassis components." International journal of fatigue 13.3 (1991): 195-205.

For many, FEA has become an essential part of maturing and qualifying design concepts, providing a cost-effective and proven basis for justifying investment in physical prototypes and testing. However, conventional fatigue analysis solutions do not work well for elastomeric components because of their macromolecular structure. In particular, the scale and combine method is not suitable for rubber parts, because of material and kinematic nonlinearities in rubber.

Rubber or elastomeric components exhibit unique behavior and require specialized analysis methods. Developing a durable elastomeric component often involves expensive, time-consuming, trial-and-error iterations. There has been a long-felt, but unsolved, need in industries such as automotive, defense, transportation, heavy equipment, offshore, medical devices and consumer products, for a solution to put developers in control of durability issues early in the development cycle, when the greatest opportunities to influence performance exists.

With regard to rubber components such as bushings, tire treads, seals, etc. used in an automotive setting, it is known that road load signals are too lengthy to use for full FEA of the rubber components. However, a full strain history remains desirable for damage calculations by FEA.

There is a continuing need for a method and system for efficiently obtaining strain and stress histories at potential failure locations in a rubber component, based on a given time-varying load data signal such as a road load input signal and FEA.

SUMMARY OF THE INVENTION

In concordance with the instant disclosure, a method and system for efficiently obtaining strain and stress histories at potential failure locations in a rubber component, based on a given a time-varying load data signal such as a road load input signal and FEA, is surprisingly discovered.

In one embodiment, a method for analyzing fatigue life of an elastomeric component includes analyzing a time-varying load data signal obtained, e.g., from measurement of the elastomeric component or from a multibody dynamics analysis of the elastomeric component. A finite element analysis of the elastomeric component is conducted to obtain a base state. A plurality of case vectors are then selected to represent a space of possible loading states that occur within the time-varying load data signal. For at least a portion of the case vectors, a finite element analysis is conducted at a plurality of discrete gridpoints along the case vectors, the gridpoints selected along the case vectors starting at the base state and tracking the case vector. Using an interpolation engine, desired local solution variables for a current state may be interpolated from the finite element analysis at the plurality of discrete gridpoints. A damage calculation may then be performed based on the desired local solution variables for the current state.

In another embodiment, a method for analyzing fatigue life by analysis of a time-varying load data signal obtained from measurement of an elastomeric component includes a step of identifying independent variables of the time-varying load data signal. A finite element analysis is then conducted to obtain a base state of the elastomeric component. A plurality of case vectors are then selected to represent a space of possible loading states that occur within the time-varying load data signal. For each of the case vectors, a finite element analysis is also conducted at a plurality of gridpoints along the case vectors, the gridpoints selected starting at the base state and tracking the case vectors. Using an interpolation engine, desired local solution variables for a desired current state are then obtained. The local solution variables provide at least one of an interpolated strain history and an interpolated stress history. A damage calculation is then performed based on the one of the interpolated strain history and the interpolated stress history, in order to determine a potential failure location in the elastomeric component.

In a further embodiment, a system for analysis of a time-varying load data signal includes an interpolation engine. The interpolation engine has at least one processor and at least one memory. The at least one memory includes a computer readable medium having a set of computer-readable instructions embodied thereon that, when executed by the at least one processor, cause the at least one processor to perform a method according to the present disclosure. In particular embodiments, the processor performs a method of: interpolating a strain history and a stress history of the elastomeric component at a current state from a simplex defined by neighboring case vectors radiating outwardly from a base state of the elastomeric component. The case vectors represent a space of possible loading states that occur within a time-varying data signal obtained from measurement of loads on the elastomeric component. The case vectors also have a plurality of discrete gridpoints disposed thereon. The interpolated strain history and the interpolated stress history may then be used in performing a damage calculation to determine fatigue life and a potential failure location in the elastomeric component.

DRAWINGS

The above, as well as other advantages of the present disclosure, will become readily apparent to those skilled in the art from the following detailed description, particularly when considered in the light of the drawings described herein.

DETAILED DESCRIPTION OF THE INVENTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the order of the steps presented is exemplary in nature, and thus, is not necessary or critical unless otherwise disclosed.

The term "road load", as is used herein, applies to any long load or displacement signal containing random content or containing varying frequency, amplitude, and phase. For example, the road load might originate from measurements made on the road, in the air, or in any type of service where there are time-varying loads on a component.

A method for analyzing road load data to select a subset for computer-aided engineering (CAE) analysis is described in U.S. Pat. Appl. Publication No. 2004/0254772 to Su, the entire disclosure of which is hereby incorporated herein by reference. A method for computing road load history from a vehicle dynamics model, using a particular approach for modeling tire behavior, is also described in U.S. Pat. No. 7,363,805 to Jayakumar et al., the entire disclosure of which is hereby incorporated herein by reference. Other suitable methods for acquiring and processing road load data or other time-varying load data may also be used within the scope of the present disclosure.

An example is made herein of an elastomeric or rubber component in the form of a simple rubber bushing in an automotive context, undergoing the time varying load in the form of the road load through operation of a vehicle having the rubber bushing. However, it should be understood that the method and system of the invention may be used to predict potential failure locations of any rubber component to which a time-varying load is applied in service, for example, a tire component, such as a rubber tread, an engine mount, a rubber seal, a rubber track, etc. Other suitable types of rubber components may also be analyzed for potential failure modes and locations using the method and system of the present disclosure.

With reference to FIGS. 1-6, a unique method and system for efficiently obtaining strain and stress histories at potential failure locations in a rubber component, such as a rubber bushing, based on a given a time-varying load data signal or road load is described.

Figure 1:
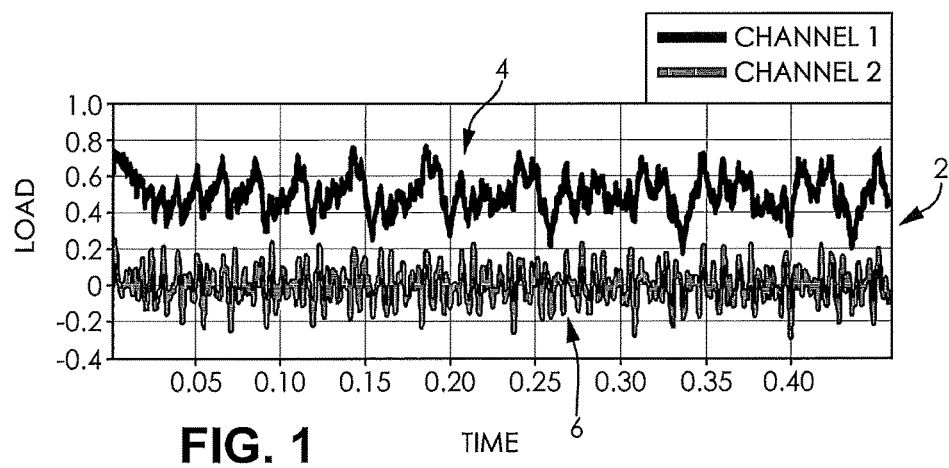
FIG. 1 is a graphical illustration of an exemplary dual channel time-varying load data signal for a rubber component undergoing a load cycle, the time-varying load data signal for use with the method and system of the present disclosure.

In FIG. 1, an illustrative example of a multi-channel road load input 2 is shown. In the example shown, the multi-channel road load input 2 is a dual channel input. The road load input 2 is time-varying, with time along a first axis, e.g., an X-axis, and the channel magnitude along a second axis, e.g., a Y-axis. However, skilled artisans should appreciate that more than two channels, providing additional dimensions to the road load input 2, and placed along different axes, may also be used within the scope of the disclosure.

The multi-channel road load input 2 is measured by sensors in the vehicle during service or computed as output from a vehicle dynamics code. As nonlimiting examples, the sensors may be load sensors and torque sensors. The sensors may be in wired or wireless communication with a data collection device (e.g., an external memory, standalone computer, networked computer, etc.) for later transmittal to the system of the disclosure, or directly in wired or wireless communication with the system of the present disclosure, as desired. One of ordinary skill in the art may select suitable sensors for providing the input 2, as desired.

In the embodiment shown in FIG. 1, the multi-channel road load input includes a first channel 4 and a second channel 6. In the case of the rubber bushing, the first channel 4 may be a radial load measured by the load sensor and the second channel may be a conical rotation measured by a torque sensor. It should be understood that any force, displacement, moment, rotation, etc., measured by other types of sensors, may also be embodied by the multi-channel road load input 2, as desired.

Figure 2:
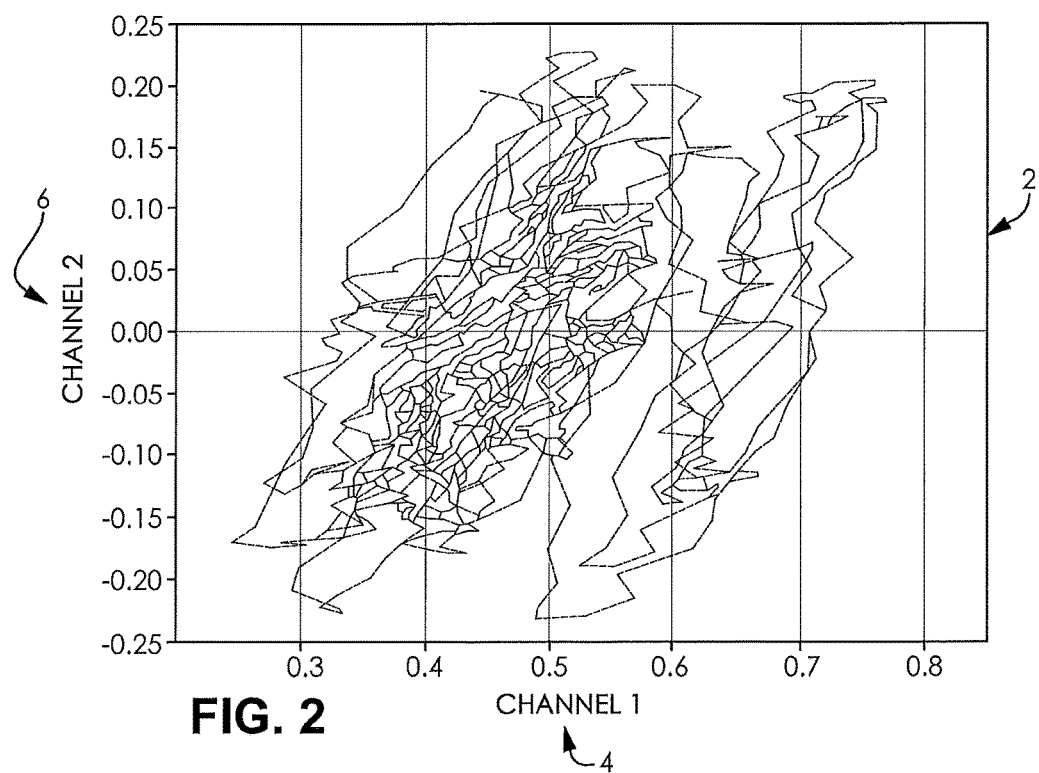
FIG. 2 is a graphical illustration of the dual channel time-varying load data signal shown in FIG. 1, with a first channel disposed along an X-axis and a second channel disposed along a Y-axis.
Figure 3:
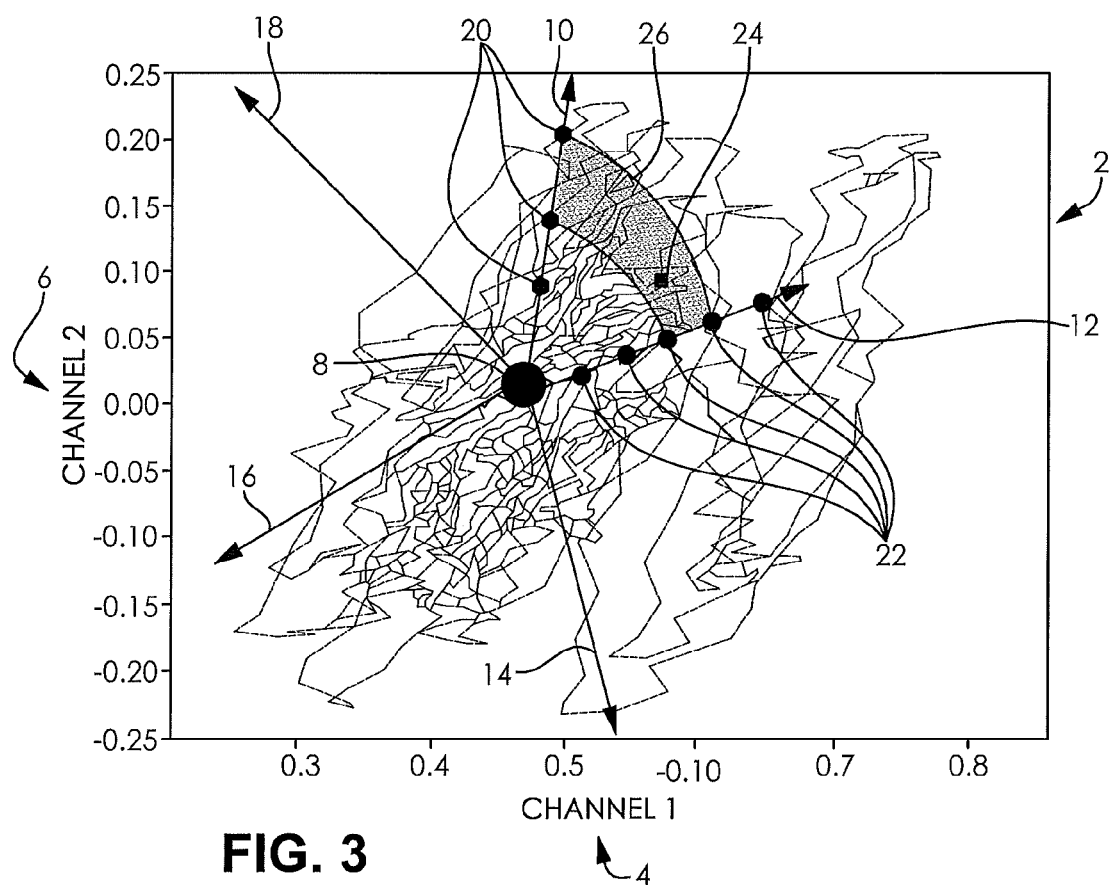
FIG. 3 is a graphical illustration of the method of the present disclosure, showing a selected base state, a series of case vectors, and a plurality of gridpoints along the case vectors which are used for an interpolation of a current state of the rubber component.

Referring now to FIG. 2, the multi-channel road load input 2 is processed into an alternate format for purposes of the analysis according to the method of the disclosure. In particular, the first channel 4 is disposed on a first axis, e.g., an X-axis, and the second channel 6 is disposed on a second axis, e.g., a Y-axis. Additional channels, if provided, are likewise placed on additional axes. It has been surprisingly found that the arrangement of data from the plurality of channels 4, 6 advantageously permits the fatigue analysis as shown in FIG. 3, and described further herein. It should also be appreciated that the arrangement of data from the plurality of channels 4, 6, as shown and described, provides certain advantages over rectangularly gridded constructs, for which convergence difficulties at grid extremes may be an issue.

Figure 4:
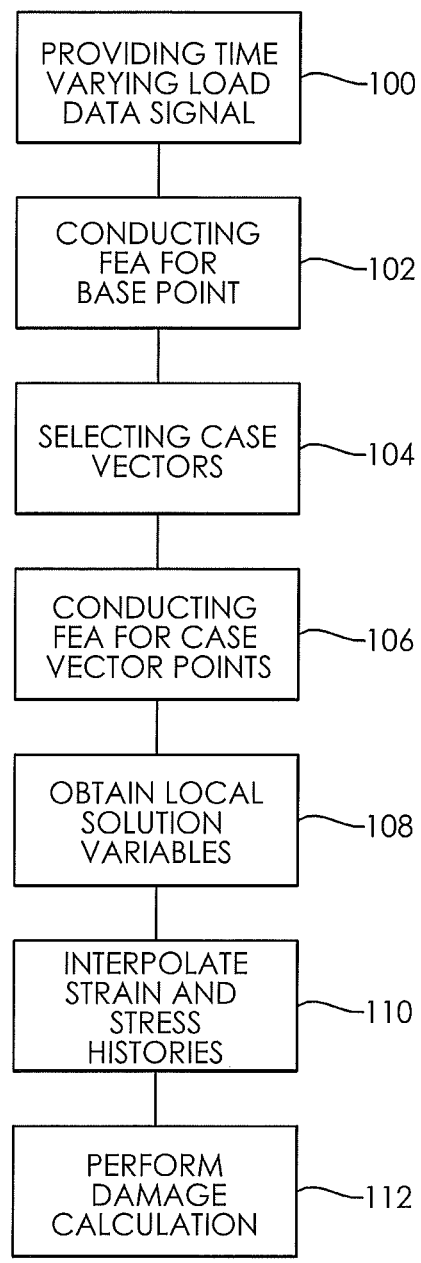
FIG. 4 is a flow chart illustration showing a method for analyzing fatigue life of a rubber component, according to one embodiment of the present disclosure.

The method of the present disclosure, as shown in FIG. 4, includes a step 100 of providing the time-varying load data signal, for example, in the form of the multi-channel road load input 2. Independent variables of the time-varying load data signal are then identified. In particular, the independent variables may be the load signal and provided by the first channel 4 and the conical rotation signal provided by the second channel 6. Advantageously, the independent variables identified are variables necessary for a subsequent damage calculation to determine a potential failure location in the elastomeric component. A skilled artisan may identify suitable independent variables for use in the damage calculation, as desired.

Based at least in part on the identified independent variables, a step 102 of conducting a finite element analysis (FEA) is performed in order to obtain a base state 8 of an elastomeric component, for example, as shown in FIG. 3. The base state 8 of the elastomeric component is modeled by FEA under simulated static or constant conditions, for example, where the elastomeric component is assumed to be under a static load. The FEA solution produces a database giving strain and stress at every point or element in the model for the given base state. One of ordinary skill in the art understands how to conduct the FEA to obtain the base state of the elastomeric component under static conditions.

In a next step 104, a plurality of case vectors 10, 12, 14, 16, 18 are then selected. The case vectors 10, 12, 14, 16, 18 represent a space of possible loading states of the elastomeric component that may occur within the time-varying load data signal. Each of the case vectors 10, 12, 14, 16, 18 begins at the base state 8, and radiate outwardly therefrom.

Although five case vectors 10, 12, 14, 16, 18 are shown in FIG. 3 for purposes of illustrating the method and system of the disclosure, it should be understood that a fewer number or a greater number of the case vectors 10, 12, 14, 16, 18, in any desired range of orientations, may also be used within the scope of the disclosure. Furthermore, the case vectors 10, 12, 14, 16, 18 may be disposed along different dimensions, which in turn may be defined by additional channel inputs, as desired.

For at least a portion of the case vectors 10, 12, 14, 16, 18, a step 106 is then performed in which a nonlinear FEA (as opposed to a "scale and combine" or linear FEA) is conducted at discrete gridpoints 20, 22 along the case vectors 10, 12, 14, 16, 18. The discrete gridpoints 20, 22 may be selected at any location on the case vectors 10, 12, 14, 16, 18 starting at the base state 8 and tracking the case vectors 10, 12, 14, 16, 18. For example, the discrete gridpoints 20, 22 may be distributed substantially evenly apart along a length of each of the case vectors 10, 12, 14, 16, 18, randomly distributed, or selectively distributed for optimum analysis with respect to a particular desired current state 24.

Figure 6:
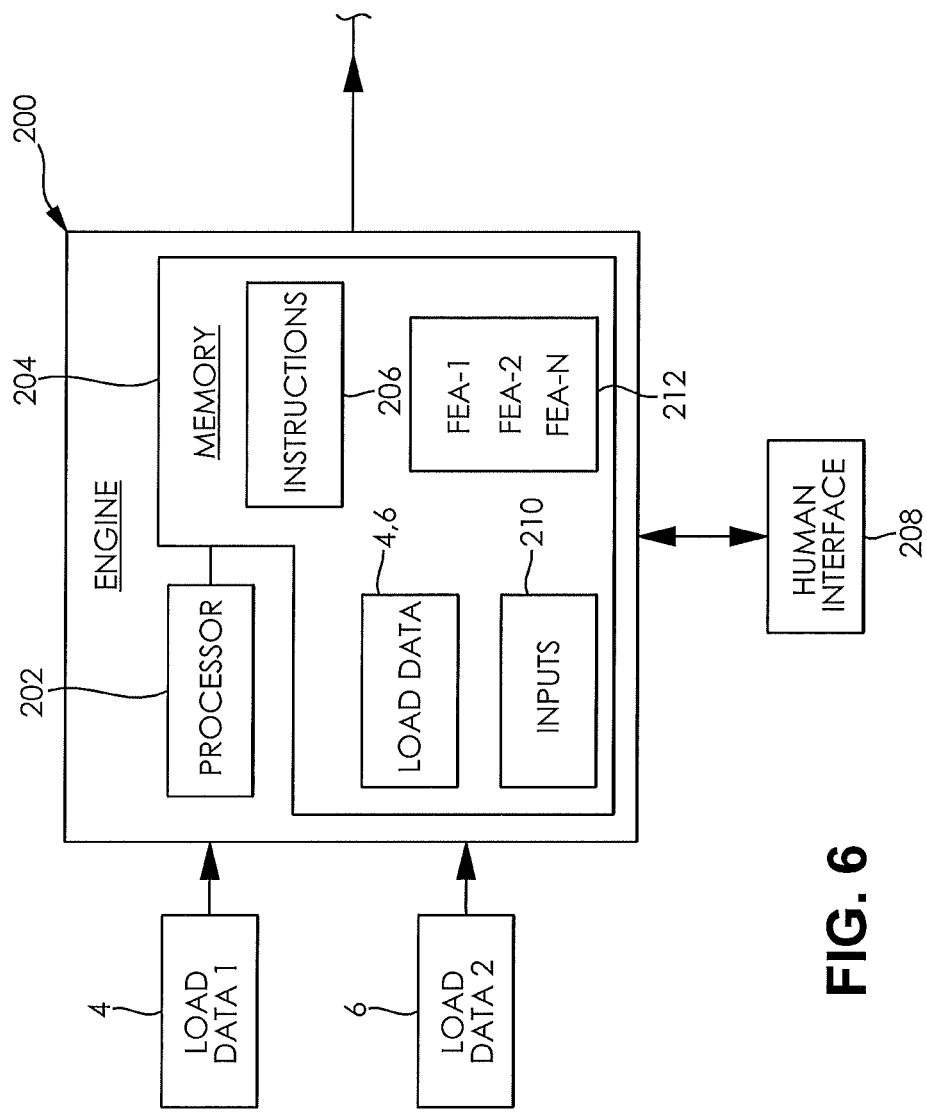
FIG. 6 is a schematic illustration of a system for analyzing fatigue life of a rubber component, according to one embodiment of the present disclosure.
Figure 6:
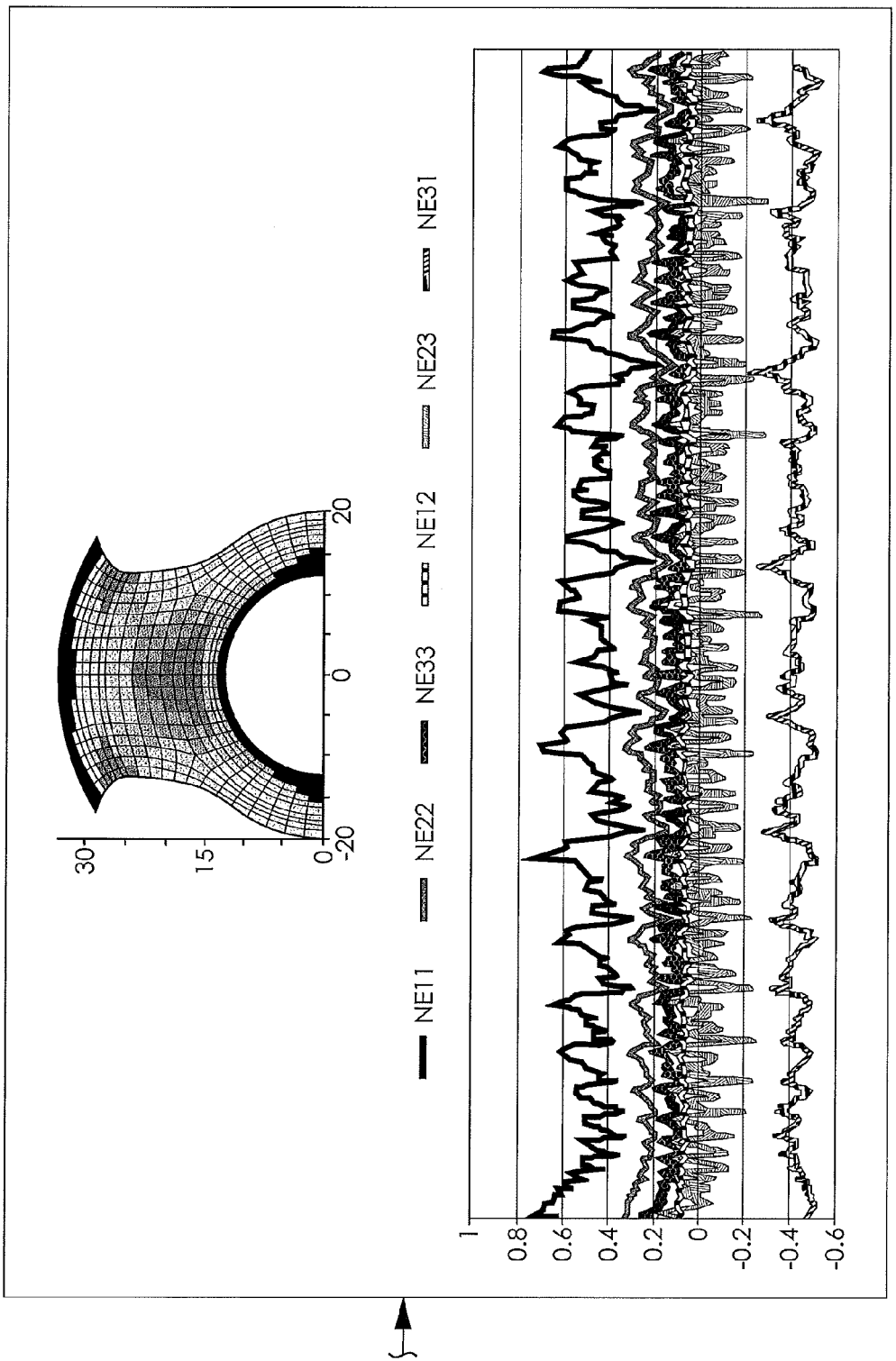

In the example shown in FIG. 3, each of the discrete gridpoints 20, 22 results in local solution variables (e.g., stresses, strains, nodal displacements, etc.) for every element from the FEAs conducted at each of the discrete gridpoints 20, 22. Any suitable number of discrete gridpoints 20, 22 may be selected along each of the case vectors 10, 12, 14, 16, 18, as desired. It should be understood that the method and system may be further refined by adding additional case vectors 10, 12, 14, 16, 18 together with modeling by FEA additional discrete gridpoints 20, 22 along the case vectors 10, 12, 14, 16, 18.

Where the discrete gridpoints 20, 22 along the case vectors have been modeled by FEA, and local solution variables obtained from the FEA at the discrete gridpoints 20, 22 in a step 108, a step 110 may then be employed to obtain desired local solution variables (e.g., strain and stress) for the desired current state 24. The step 110 is performed by an interpolation engine 200 reading output from the FEA, for example, as shown in FIG. 6 and described further herein below. In particular, the desired local solution variables permit an interpolation of strain history and stress history for the modeled elastomeric component in a step 110.

Figure 5:
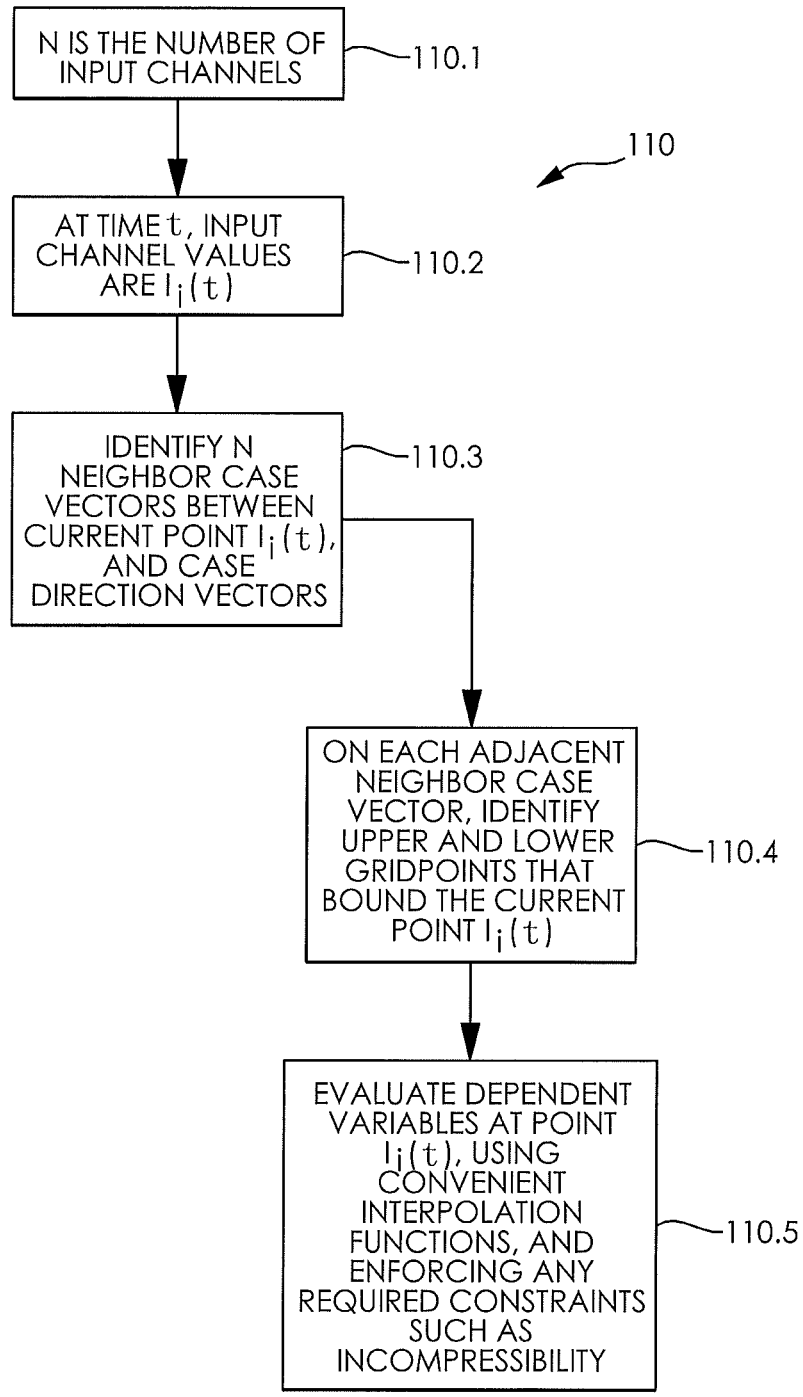
FIG. 5 is a flow chart illustration showing a further method for interpolating of strain and stress histories as part of the method shown in FIG. 4.

Referring now to FIG. 5, a suitable method for obtaining the desired local solution variables for the desired current state 24 is shown in steps 110.1 to 110.5. For example, in step 110.1, the number of input channels 4, 6 is determined and assigned variable (N). In step 110.2, the desired current state 24 as a function of time is assigned a value $I_i(t)$, where (I) is the value of the input channel, (i) is the channel, and time is the variable (t).

In step 110.3, the case vectors 10, 12 that neighbor the desired current state 24, $I_i(t)$ are identified. As a nonlimiting example, the neighboring case vectors 10, 12 may be the nearest of the case vectors 10, 12, 14, 16, 18 to the desired current state 24, $I_i(t)$. However, it should be understood that certain case vectors 10, 12, 14, 16, 18 not necessarily the nearest to the desired current state 24, $I_i(t)$ may also be selected within the scope of the disclosure.

An interpolation cell 26, bounded by an upper and lower simplex defining the interpolation cell 26, with edges that include the neighboring case vectors 10, 12, is then identified in step 110.4. It should be appreciated that the use of simplices permit a formation of the interpolation cell 26 in any number of dimensions defined by any number of channels. The identification of the interpolation cell 26 in step 110.4 is conducted by identifying upper and lower discrete gridpoints 20, 22 on the neighboring case vectors 10, 12, that bound the desired current state 24, $I_i(t)$.

Where the interpolation cell 26 has been identified, it should be understood that the dependent variables at the desired current state 24, $I_i(t)$ may be evaluated in a step 110.5, for example, using convenient interpolation functions (e.g., piecewise constant interpolation, linear interpolation, polynomial interpolation, spline interpolation, etc.). Once the interpolation cell 26 has been identified, other forms of interpolation including non-linear interpolation and combinations of different interpolation strategies may also be used, as desired. The desired current state 24, $I_i(t)$ is thereby interpolated.

It should be appreciated that, in evaluating the dependent variables at the desired current state 24, $I_i(t)$, constraints such as incompressibility may also be enforced. Such constraints generally cause the results to comply with real-world limitations, and may be selected by a skilled artisan, as desired.

In a step 112, a damage calculation based the interpolated strain history and/or the interpolated stress history to determine fatigue life and a potential failure location in the elastomeric component at the desired current state 24 is then performed. In one example, the damage calculation may be performed as described in U.S. Pat. No. 6,634,236 to Mars, the entire disclosure of which is hereby incorporated herein by reference. Other means for performing the damage calculation using the interpolated strain history and the interpolated stress history may also be employed within the scope of the present disclosure.

With renewed reference to FIG. 6, the interpolation engine 200 of the present disclosure is shown. The interpolation engine 200 is provided for analysis of the time-varying load data signal obtained from measurement of the elastomeric component in service. The interpolation engine includes at least one processor 202 and at least one memory 204. The at least one memory 204 may be in the form of a tangible, non-transitory computer readable medium having a set of computer-readable instructions 206 embodied thereon. The instructions 206, when executed by the at least one processor 202, cause the at least one processor 202 to perform the method of the present disclosure.

The memory 204 of the interpolation engine 200 includes at least one internal database. The internal database of the memory 204 has a unique structure. For each finite element, a base state (both independent and dependent variables) is stored in the database. For each case vector 10, 12, 14, 16, 18 computed by the processor 202, the unit vector of the case vector 10, 12, 14, 16, 18 is also stored in the database. For each discrete case vector gridpoint 20, 22, independent variables (e.g., a first parameter and a second parameter) and dependent variables (e.g., strain tensor components and nodal displacements) are also stored in the database.

In particular embodiments, the at least one processor 202 is configured to obtain the desired local solution variables for each point or element from the FEA of the elastomeric component based on the time-varying load data signal, i.e., the multi-channel road input 2 including the first channel 4 and the second channel 6, as described further hereinabove.

The at least one processor is also configured to provide at least one of the interpolated strain history and the interpolated stress history for further use in performing the damage calculation to determine the fatigue life and potential failure location in the elastomeric component. For example, as shown in FIG. 6, interpolated components of nominal strain tensors (NE) as a function of time may be the output of the interpolation engine 200. It should be appreciated that the interpolation of the system and method is particularly efficient, as opposed to running the finite element model through an entirety of the road load input is prohibitively time-consuming.

The instructions 206 for execution by the at least one processor 202 may also be used to perform the other various steps of the method of the present disclosure, or permit the user to perform various steps, as detailed further hereinabove.

The processor 202 may also be in communication with a human interface 208, for example, at least one of a keyboard, a mouse, a video screen, a touch screen, and the like. The human interface 208 permits a user to interact with the interpolation engine 200, for example, by providing inputs 210 for the selection of suitable case vectors 10, 12, 14, 16, 18 and the creation of the plurality of FEA models 212 in accordance with the disclosed method. The human interface 208 may also permit the user to upload the time-varying load data from measurements of the elastomeric component to the system. Other interactions between the user and the system as described hereinabove may be facilitated through use of the human interface 208.

In other embodiments, the time-varying load data may be uploaded to the system through a wired or wireless connection. For example, the system may be in communication with a computer network such as the Internet, through which the time varying load data is transmitted to the system. In another example, the time varying load data in the form of the first channel 4 and the second channel 6, saved from testing of the elastomeric component, may be uploaded to the system from a memory device such as a USB drive or the like. Other means for uploading the time-varying load data to the system may also be used within the scope of the present disclosure.

Advantageously, the method and system of the present disclosure provides a way to estimate local history of stress and strain, based on FEA modeling of a series of load cases. It is adapted for the typical case where dynamic load perturbations are imposed on top of a static loaded state. The method and system works with any number of independent input channels, and dependent local solution variables.

It is surprisingly found that the method and system of the disclosure avoids a need to model full time history in FEA. It accounts properly for material and kinematic nonlinear behavior, which is a feature not found in other known failure analysis methods and systems. Moreover, the present method and system interpolates within a multidimensional space (e.g., one dimension for each input channel), which permits interpolation accuracy to be increased incrementally by adding additional case vectors.

While certain representative embodiments and details have been shown for purposes of illustrating the invention, it will be apparent to those skilled in the art that various changes may be made without departing from the scope of the disclosure, which is further described in the following appended claims.

What is claimed is:

1. A method for analyzing fatigue life of an elastomeric component, the method including steps operated by a system including a user interface and an interpolation engine, the interpolation engine in communication with the user interface, and the interpolation engine including at least one processor and at least one memory having a tangible, non-transitory computer readable medium, the system further including a first sensor and a second sensor in communication with the elastomeric component, and a data collection device in communication with the first sensor and the second sensor, the first sensor configured to measure a time-varying first variable of the elastomeric component during dynamic loading to provide a first channel of a multichannel input, wherein the first sensor is a load sensor and the first variable is a load, the second sensor configured to measure a time-varying second variable of the elastomeric component during the dynamical loading to provide a second channel of the multi-channel input, wherein the second variable is one of an other load, a force, a displacement, a moment, and a rotation, and the data collection device configured to receive the multi-channel input from the first sensor and the second sensor, and to supply the multi-channel input to the interpolation engine, the steps comprising:

receiving, by the interpolation engine from the data collection device, a base finite element analysis (FEA) with a base state of the elastomeric component, the base state of the elastomeric component obtained by analyzing the elastomeric component including at least one of stress and strain for at least one element from the base FEA of the elastomeric component under simulated static conditions;

generating, by the interpolation engine, a predictive model including the multi-channel input, the base state from the base FEA of the elastomeric component under simulated static conditions, and generated case vectors to represent a space of loading states that occur within the multi-channel input, the case vectors originating at and extending outwardly from the base state in the predictive model, the case vectors including a set of case vectors neighboring a desired current state in the predictive model, the predictive model further including an interpolation cell that bounds the desired current state, the interpolation cell having edges that include the set of the case vectors neighboring the desired current state; and for the set of the case vectors neighboring the desired current state in the predictive model, receiving by the interpolation engine from the user interface a plurality of additional FEA of the elastomeric component under simulated dynamic conditions at a plurality of discrete gridpoints along the set of the case vectors neighboring the desired current state, starting at the base state and tracking the set of the case vectors neighboring the desired current state;

obtaining, by the interpolation engine, local solution variables from the additional FEA of the elastomeric component at each of the plurality of discrete gridpoints, the local solution variables including at least one of stress and strain for at least one element from the additional FEA for each of the plurality of discrete gridpoints, wherein the interpolation engine has a database included in the at least one memory that store the base FEA used to obtain the base state of the elastomeric component and each of the additional FEA used to obtain the local solution variables at each of the discrete gridpoints, wherein the predictive model generated by the interpolation engine is different from the base FEA and the additional FEA;

interpolating, by the interpolation engine, using the local solution variables associated with the interpolation cell and an interpolation function, at least one of a strain history and a stress history of the elastomeric component at the desired current state; and performing, by a set of instructions embodied on the at least one memory of the interpolation engine and executed by the at least one processor, a damage calculation based on one of the strain history and the stress history interpolated for the elastomeric component, whereby the fatigue life of the elastomeric component is predicted.

2. The method of claim 1, including a step of evaluating a nonlinear, multiaxial relationship between loads and one of strains and stresses for application in situations where linear superposition of unit load solutions does not apply because of material, kinematic or other nonlinearity in the solutions.

3. The method of claim 2, including a step of defining by a nonlinear solution a discretization of the relationship between the loads and the one of the strains and stresses at the discrete gridpoints on each of the case vectors.

4. The method of claim 3, wherein the discretization of the relationship between the loads and the one of the strains and stresses is refined by an incremental addition of new case vectors.

5. The method of claim 1, wherein the case vectors extend in two or more dimensions from the base state.

6. The method of claim 1, wherein the set of case vectors neighboring the desired current state and interpolation weighting functions are evaluated and stored in the memory of the interpolation engine, prior to evaluation for each finite element, for purposes of enhanced execution speed.

7. The method of claim 1, further comprising the step of making another elastomeric component with a parameter modified in response to the fatigue life prediction.

8. The method of claim 1, wherein the second sensor is a torque sensor and the second variable is a time-varying torque of the elastomeric component during the dynamical loading.

9. A system for analyzing fatigue life of an elastomeric component, comprising:
a user interface; and
an interpolation engine in communication with the user interface, and the interpolation engine including at least one processor and at least one memory having a tangible, non-transitory computer readable medium;

a first sensor and a second sensor in communication with the elastomeric component, the first sensor configured to measure a time-varying first variable of the elastomeric component during dynamic loading to provide a first channel of a multichannel input, wherein the first sensor is a load sensor and the first variable is a load, the second sensor configured to measure a time-varying second variable of the elastomeric component during the dynamical loading to provide a second channel of the multi-channel input, wherein the second variable is one of an other load, a force, a displacement, a moment, and a rotation; and a data collection device in communication with the first sensor and the second sensor, the data collection device configured to receive the multi-channel input from the first sensor and the second sensor, and to supply the multi-channel input to the interpolation engine, the interpolation engine performing the steps comprising:

receiving, by the interpolation engine from the data collection device, a base finite element analysis (FEA) with a base state of the elastomeric component, the base state of the elastomeric component obtained by analyzing the elastomeric component including at least one of stress and strain for at least one element from the base FEA of the elastomeric component under simulated static conditions;

generating, by the interpolation engine, a predictive model including the multi-channel input, the base state from the base FEA of the elastomeric component under simulated static conditions, and generated case vectors to represent a space of loading states that occur within the multi-channel input, the case vectors originating at and extending outwardly from the base state in the predictive model, the case vectors including a set of case vectors neighboring a desired current state in the predictive model, the predictive model further including an interpolation cell that bounds the desired current state, the interpolation cell having edges that include the set of the case vectors neighboring the desired current state; and for the set of the case vectors neighboring the desired current state in the predictive model, receiving by the interpolation engine from the user interface a plurality of additional FEA of the elastomeric component under simulated dynamic conditions at a plurality of discrete gridpoints along the set of the case vectors neighboring the desired current state, starting at the base state and tracking the set of the case vectors neighboring the desired current state;

obtaining, by the interpolation engine, local solution variables from the additional FEA of the elastomeric component at each of the plurality of discrete gridpoints, the local solution variables including at least one of stress and strain for at least one element from the additional FEA for each of the plurality of discrete gridpoints, wherein the interpolation engine has a database included in the at least one memory that store the base FEA used to obtain the base state of the elastomeric component and each of the additional FEA used to obtain the local solution variables at each of the discrete gridpoints, wherein the predictive model generated by the interpolation engine is different from the base FEA and the additional FEA;

interpolating, by the interpolation engine, using the local solution variables associated with the interpolation cell and an interpolation function, at least one of a strain history and a stress history of the elastomeric component at the desired current state; and performing, by a set of instructions embodied on the at least one memory of the interpolation engine and executed by the at least one processor, a damage calculation based on one of the strain history and the stress history interpolated for the elastomeric component, whereby the fatigue life of the elastomeric component is predicted.

10. The method of claim 1, wherein the interpolation engine further generates a graphical illustration of the predictive model at the user interface, the graphical illustration including a grid with the first channel along a first axis, and the second channel along a second axis, the base state identified on the grid and having the generated case vectors radiating outwardly therefrom, the discrete gridpoints shown on the set of the case vectors neighboring the desired current state, and the desired current state shown disposed within the interpolation cell having the edges that include the set of the case vectors neighboring the desired current state.

11. The system of claim 9, wherein the interpolation engine further generates a graphical illustration of the predictive model at the user interface, the graphical illustration including a grid with the first channel along a first axis, and the second channel along a second axis, the base state identified on the grid and having the generated case vectors radiating outwardly therefrom, the discrete gridpoints shown on the set of the case vectors neighboring the desired current state, and the desired current state shown disposed within the interpolation cell having the edges that include the set of the case vectors neighboring the desired current state.

12. The system of claim 9, further comprising the step of making another elastomeric component with a parameter modified in response to the fatigue life prediction.

13. The system of claim 9, wherein the second sensor is a torque sensor and the second variable is a time-varying torque of the elastomeric component during the dynamical loading.

* * * * *